United States Patent
Reid et al.

(10) Patent No.: US 7,521,219 B2
(45) Date of Patent: Apr. 21, 2009

(54) METHOD OF PRODUCING BACULOVIRUS

(75) Inventors: Steven Reid, Brisbane (AU); Linda Lua, Brisbane (AU)

(73) Assignee: The University of Queensland, Brisbane, Queensland (AU)

( * ) Notice: Subject to any disclaimer, the term of this patent is extended or adjusted under 35 U.S.C. 154(b) by 23 days.

(21) Appl. No.: 10/578,197

(22) PCT Filed: Nov. 10, 2004

(86) PCT No.: PCT/AU2004/001549

§ 371 (c)(1),
(2), (4) Date: Jun. 13, 2006

(87) PCT Pub. No.: WO2005/045014

PCT Pub. Date: May 19, 2005

(65) Prior Publication Data

US 2007/0111295 A1    May 17, 2007

(30) Foreign Application Priority Data

Nov. 10, 2003    (AU) .............................. 2003906171

(51) Int. Cl.
*C12N 7/00*     (2006.01)
*C12N 7/02*     (2006.01)
*C12N 7/06*     (2006.01)
*A01N 63/00*    (2006.01)

(52) U.S. Cl. ..................... 435/235.1; 435/238; 435/239

(58) Field of Classification Search .................. None
See application file for complete search history.

(56) References Cited

OTHER PUBLICATIONS

Volkman et al., J. Virol., 1976, vol. 19, No. 3, pp. 820-832.*
Chakraborty, S. and Reid, S., 1999, Serial passage of a *Helicoverpa armigera* nucleopolyhedrovirus in *Helicoverpa zea* cell cultures, Journal of Invertebrate Pathology, 73: 303-308.
Slavicek, J.M. et al., 1996, Isolation of a baculovirus variant that exhibits enhanced polyhedra production stability during serial passage in cell culture, Journal of Invertebrate Pathology, 67: 153-160.
Wong, K.T.K. et al., 1996, Low multiplicity infection of insect cells with a recombinant baculovirus: the cell yield concept, Biotechnology and Bioengineering, 49: 659-666.
Chakraborty, S. et al., 1995, In vitro production of wild type Heliothis baculoviruses for use as biopesticides, Australasian Biotechnology, 5: 82-86.
Lua, L.H.L. et al., 2002, Phenotypic and genotypic analysis of *Helicoverpa armigera* nucleopolyhedrovirus serially passaged in cell culture, Journal of General Virology, 83: 945-955.
Bull, J.C. et al., (Apr. 2003), A few-polyhedra mutant and wild-type nucleopolyhedrovirus remain as a stable polymorphism during serial coinfection in *Trichoplusia ni*, Applied and Environmental Microbiology, 69: 2052-2057.

* cited by examiner

*Primary Examiner*—David Guzo
(74) *Attorney, Agent, or Firm*—Shoemaker and Mattare

(57) ABSTRACT

The present invention is directed to a method for producing commercial quantities of baculovirus using a combination of methods involving producing occlusion bodies with infectious baculovirus in caterpillar larvae and large numbers of viral particles with serial passages in cell culture. A two step method was developed by initially producing infectious virus in caterpillar larvae and then using the resultant infectious virus as an inoculum for a limited number of serial passages in cell culture so to produce large amounts of infectious baculovirus.

10 Claims, 5 Drawing Sheets

FIG. 1

OB Stock Virus

OB original source: Larvae or cell culture cloned ⇒ Larvae 1.7x10$^{10}$ OB per larvae ⇒ OB Master Stock 10$^{11}$ OB Stable at 4 °C for 10 years OB from Master Stock ⇒ 30 larva required per year ⇒ OB Working Stock 5x10$^{11}$ OB (sufficient for 20 runs/year)

ODV Extraction per run

OB from Working Stock 2.5x10$^{10}$ OB required —Extraction→ ODV —Infection→ 10L Bioreactor 5x10$^5$ cells/ml → Remove cells → BV 10L at 10$^7$ PFU/ml Stable at 4°C for 1 week while titre → PRODUCTION

FIG. 2

VPM3 MEDIA FORMULATION

SALTS

| Component | VPM 3 (MG/L) | VPM* (MG/L) |
|---|---|---|
| $CaCl_2$ | 500 | 500 |
| $CoCl_2.6H_2O$ | 0.05 | 0.05 |
| $CuCl_2.2H_2O$ | 0.20 | 0.20 |
| $FeSO_4.7H_2O$ | 1.70 | 1.70 |
| KCl | 1,200 | 1,200 |
| $MgSO_4$ | 918 | 918 |
| $MnCl_2.4H_2O$ | 0.02 | 0.02 |
| NaCl | 2,700 | 2,700 |
| $NaHCO_3$ | 350 | 350 |
| $NaH_2PO_4.H_2O$ | 1,160 | 1,160 |
| $(NH_4)_6Mo_7O_{24}.4H_2O$ | 0.04 | 0.04 |
| $ZnSO_4.7H_2O$ | 0.04 | 0.04 |

SUGARS

| Component | VPM 3 (MG/L) | VPM* (MG/L) |
|---|---|---|
| Glucose | 8,000 | 8,000 |
| Sucrose | 3,000 | 3,000 |
| Maltose | 500 | 500 |
| Trehalose * | 500 | 0 |
| Galactose * | 300 | 0 |

AMINO ACIDS

| Component | VPM 3 (MG/L) | VPM* (MG/L) |
|---|---|---|
| L-Cystine.2HCl | 200 | 200 |
| L-Lysine.HCl | 300 | 300 |
| L-Methionine | 200 | 200 |
| L-Asparagine | 300 | 300 |
| L-Glutamic Acid (Na) | 3,000 | 3,000 |
| L-Glutamic Acid (K) | 3,000 | 3,000 |
| Hy Pep Dev 4602 | 750 | 750 |

VITAMINS

FIG. 2 continued

| Component | VPM 3 (MG/L) | VPM* (MG/L) |
|---|---|---|
| Inosine | 200 | 200 |
| Choline Chloride | 10 | 10 |
| Vitamins IPL-41 (100X) | 10 ml | 10 ml |

HYDROLYSATES

| Component | VPM 3 (MG/L) | VPM* (MG/L) |
|---|---|---|
| Yeast Extract | 3,000 | 3,000 |
| Primatone | 2,500 | 2,500 |
| Hy Soy | 500 | 500 |
| Casein | 500 | 500 |
| Lactalbumin (Edamin S) | 500 | 500 |

OTHER COMPONENTS

| Component | VPM 3 (MG/L) | VPM* (MG/L) |
|---|---|---|
| Dextran T 10 * | 50 | 0 |
| Chitosin * | 2.5 | 0 |
| Glutathione (Reduced Na) | 10 | 10 |
| Glycerol | 2,000 | 2,000 |

LIPIDS

| Component | VPM 3 (MG/L) | VPM* (MG/L) |
|---|---|---|
| Cholesterol | 4.5 | 4.5 |
| Cod Liver Oil | 12.5 | 12.5 |
| Vitamin E acetate | 3 | 3 |
| Tween 80 | 25 | 25 |
| Lecithin (Soya) * | 4 | 0 |
| ETOH (ml) | 1.25 | 1.25 |
| Pluronic Polyol F-68 | 900 | 900 |

Specifications:
pH: 6.2-6.3
Osmolarity: 355-375 mOsm/kg

VPM3 and VPM* are low cost serum-free media that we have trialled for the ODV extraction process and subsequent passages. These media are similar but not identical to baculovirus/insect cell culture media reported in the literature. The additives indicated with an asterisk are unique additives by us into VPM3. VPM3 works better than VPM* for the extraction process. Further optimisation of the media for the ODV extraction process

FIG. 3

Table 1: Virus yield data of different ODV extractions

| Number of OB used for extraction | Yield at passage 4 (OB per cell) |
|---|---|
| $5 \times 10^9$ (100 OB per cell) | 283 |
| $2.5 \times 10^9$ (50 OB per cell) | 352 |
| $1 \times 10^9$ (20 OB per cell) | 369 |
| $5 \times 10^8$ (10 OB per cell) | 339 |
| $2.5 \times 10^8$ (5 OB per cell) | 383 |

METHOD OF PRODUCING BACULOVIRUS

FIELD OF INVENTION

The present invention relates to the production of baculoviruses and in particular a method of producing commercial quantities of baculoviruses.

PRIOR ART

Baculoviruses have been used for a variety of applications including the production of recombinant proteins and use as biopesticides. The problem with commercially using baculoviruses has been the inability to produce large amounts of infectious baculovirus.

Economic commercial production of baculoviruses requires production of at least 10,000 litre culture with a virus yield greater than 150 OB (occlusion bodies) per cell (Greenfield, P. F., Reid, S., Weiss, S. & Scholz, B. (1999). Baculoviruses as biological control agents: research, production and commercial issues. In *The 5th Asia-Pacific Biochemical Engineering Conference Proceedings*. Phuket, Thailand). The standard scale-up process for large scale baculovirus production requires up to 5 passages of baculovirus in cell culture to obtain enough virus for a frozen Baculovirus working stock. A further 6 passages are required to scale-up the production process to 10,000 litre scale in order to achieve economical production (Rhodes, D. J. (1996). Economics of baculovirus-insect cell production systems. *Cytotechnology* 20, 291-297). According to this standard scale-up process, it will take 11 passages to obtain the final virus product at 10,000 litre scale, assuming that the virus is stable during serial passaging and is still producing more than 150 OB per cell.

Baculoviruses however are not stable during serial passaging in cell culture as they appear to mutate spontaneously to form FP (few polyhedra) mutants or DIP (defective interfering particles) mutants. FP mutants accumulate rapidly in cell culture due to spontaneous mutations in the 25K FP gene of the viral genome. For HaSNPV, FP mutation is so rapid that by passage 6, the entire virus population is composed of FP mutants. The yield is below 10 OB per cell and the OB produced are not biologically active (Lua, L. H. L., Pedrini, M., Reid, S., Robertson, A. & Tribe, D. E. (2002). Phenotypic and genotypic analysis of *Helicoverpa armigera* nucleopolyhedrovirus serially passaged in cell culture. *Journal of General Virology* 83, 947-957). Similarly DIPs can also accumulate rapidly during serial passaging of Baculoviruses with high MOIs in cell culture. DIPs of AcMNPV infection have been detected as early as passage 4 when an MOI of 10 PFU per cell was used. DIPs are the result of large deletions in the virus genome. DIPs require a 'helper virus' (wild-type virus) for replication (Pijlman, G. P., van den Born, E., Martens, D. E. & Vlak, J. M. (2001). *Autographa californica* baculoviruses with large genomic deletions are rapidly generated in infected insect cells. *Virology* 283, 132-138). The occurrence of these mutations cause problems during the scale-up from virus inoculum to large scale production.

FP mutation during serial passaging of HaSNPV poses a greater threat to scale-up of a production process than does the appearance of DIPs. FP mutations occur much faster and earlier than DIPs, regardless of the MOI.

In cell culture, there does not appear to be any selection pressure for infectious OB. FP mutant infected cells bud more baculovirus than MP (many polyhedra) infected cells thereby providing a selective advantage for FP mutants. In larvae and unlike in cell. culture, infectious OB have a selective advantage in being the form of baculovirus transmitted to other larvae (Potter, K. N., Jaques, R. P. & Faulkner, P. (1978). Modification of *Trichoplusia ni* nuclear polyhedrosis virus passaged in vivo. *Intervirology* 9, 76-85).

Serial passaging may produce large amounts of baculovirus but the virus is not infectious. Production of large quantities of virus from caterpillar larvae is impractical because of the large numbers of larvae required and difficulties in subsequent large scale purification necessary to isolate the virus. Methods of extracting occlusion derived virus from occlusion bodies after each passage during large volume production is also very difficult technically and impractical. It would be necessary for the occlusion bodies to be extracted from the cells and concentrated after each passage while maintaining sterility during the whole process.

At present, there are no methods of economically producing large commercial quantities of infectious baculovirus.

OBJECT OF THE INVENTION

It is an object of the present invention to provide an alternative method of producing large quantities of baculovirus.

SUMMARY OF THE INVENTION

The present invention was conceived and reduced to practice by the need to produce commercial quantities of infective baculovirus OB. The present invention was conceived by identifying the advantage of producing occlusion bodies with infectious baculovirus in caterpillar larvae and large numbers of viral particles with serial passages in cell culture. A two step method was then developed by initially producing infectious virus in caterpillar larvae and then using the resultant infectious virus as an inoculum for a limited number of serial passages in cell culture so to produce large amounts of infectious baculovirus.

In one aspect the present invention resides in a method of producing large quantities of baculovirus including inoculating caterpillar larvae with a baculovirus inoculum;

incubating inoculated caterpillar larvae;

harvesting baculovirus occlusion bodies from the infected caterpillar larvae;

extracting occlusion derived virus from the occlusion bodies;

inoculating a culture of host insect cells with an inoculum of occlusion derived virus;

incubating virus/cell culture; and harvesting baculovirus from the incubated virus/cell culture.

The incubation of the virus/cell culture is preferably for a period of time that enables four or five passages of baculovirus.

Baculovirus is used in the specification as a general term encompassing different baculovirus species including *Helicoverpa armigera* SNPV, *Helicoverpa zea* SNPV, *Spodoptera frugiperda* MNPV, *Anticarsia gemmatalis* MNPV, *Autographa californica* MNPV, *Anagrapha falcifera* MNPV, *Lymantria dispar* MNPV, *Bombyx mori* MNPV, *Spodoptera exigua* MNPV, *Trichoplusia ni* MNPV, *Orgyia pseudotsugata* MNPV and *Buzura suppressaria* SNPV. A preferred baculovirus is a *Helicoverpa armigera* isolate. A preferred *Helicoverpa armigera* isolate is strain H25EA1.

The original baculovirus inoculum may be derived from any suitable source including occlusion bodies from larvae or cell culture.

There may be more than one step of producing baculovirus from larvae in order to produce a suitable amount of occlusion bodies working stock. In one preferred form, baculovirus may be produced from larvae in an initial step to form an occlusion bodies master stock. The occlusion bodies master stock may then be used to provide inoculum for the production of occlusion bodies working stocks. In a preferred form, an occlusion bodies working stock preferably has approximately $2 \times 10^{12}$ occlusion bodies whereas occlusion bodies master stock has approximately $10^9$ occlusion bodies. Both the master stock and working stock may be stored at 4 degrees Celsius or frozen.

Preferably the occlusion derived virus (ODV) is inoculated in the cell culture at a relatively high MOI. In a preferred embodiment, an inoculum of occlusion derived virus is obtained from as low as $2.5 \times 10^{10}$ occlusion bodies and introduced into a ten litre bioreactor containing $5 \times 10^5$ cells per ml. The culture is progressively scaled up from a 10 litre volume (P1) to a 100 litre volume (P2), then to a 1,000 litre volume (P3) and finally a 10,000 litre volume (P4). The 10 litre culture produces approximately $10^7$ PFU (Baculovirus) per ml. The 10,000 litre culture preferably has an approximate cell density between $1.5$-$2.0 \times 10^9$ cells per litre and a $2.5 \times 10^{11}$ OB per litre (which is approximately 150 OB per cell). The OB have a LC50 against heliothis caterpillars of 0.2-1.0 OB per $mm^2$.

The extraction of the occlusion derived virus from the working stock may occur by any suitable method. Occlusion derived virus is preferably extracted using alkali to lyse the occlusion bodies and the resultant viral particles are stabilized in an appropriate buffering media. The preferred method of extraction includes mixing an alkaline solution with an OB suspension and incubating the mixture for a period of time and at a temperature that separates the viral particles. The ODV are then preferably suspended in a stabilizing media preferably VPM3 (disclosed in FIG. 2). Preferably no acid neutralization step is included. The preferred ODV extraction method is the VPM3 extraction method outlined below. The VPM3 extraction method has the advantages that it does not use a trypsin treatment and VPM3 media does not contain serum thus making the method more economical than the conventional methods and therefore more suitable for large scale commercial production.

In another aspect the invention broadly resides in the Baculovirus product produced from the above mentioned method. The Baculovirus product is characterized by being the amount of infectious baculovirus of approximately $2.5 \times 10^{15}$ OB with a LC50 against *Helicoverpa* spp caterpillars of 0.2-1.0 OB per $mm^2$. This quantity of infectious Baculovirus has not previously been obtainable from a single in vitro method of production. A further advantage is that this quantity of infectious Baculovirus is economically producible.

The resultant Baculovirus can be used for a variety of purposes including as a biopesticide. By way of example *Helicoverpa armigera* OB can be applied to crops at $5 \times 10^{11}$ to $5 \times 10^{12}$ OB per Ha to ensure control of the *H. armigera* caterpillar pest.

BRIEF DESCRIPTION OF THE DRAWINGS

In order that the present invention be more readily understood and put into practical effect, reference will now be made to the accompanying drawings wherein:

FIG. 1 is a diagrammatic representation of the method of producing large amounts of Baculovirus;

FIG. 2 shows the formulation of the extraction stabilization media VPM3 of the preferred embodiment;

FIG. 3 compares the number OB used for extraction and resultant OB per cell at passage 4.

DETAILED DESCRIPTION OF THE PREFERRED EMBODIMENT

Figure 4:
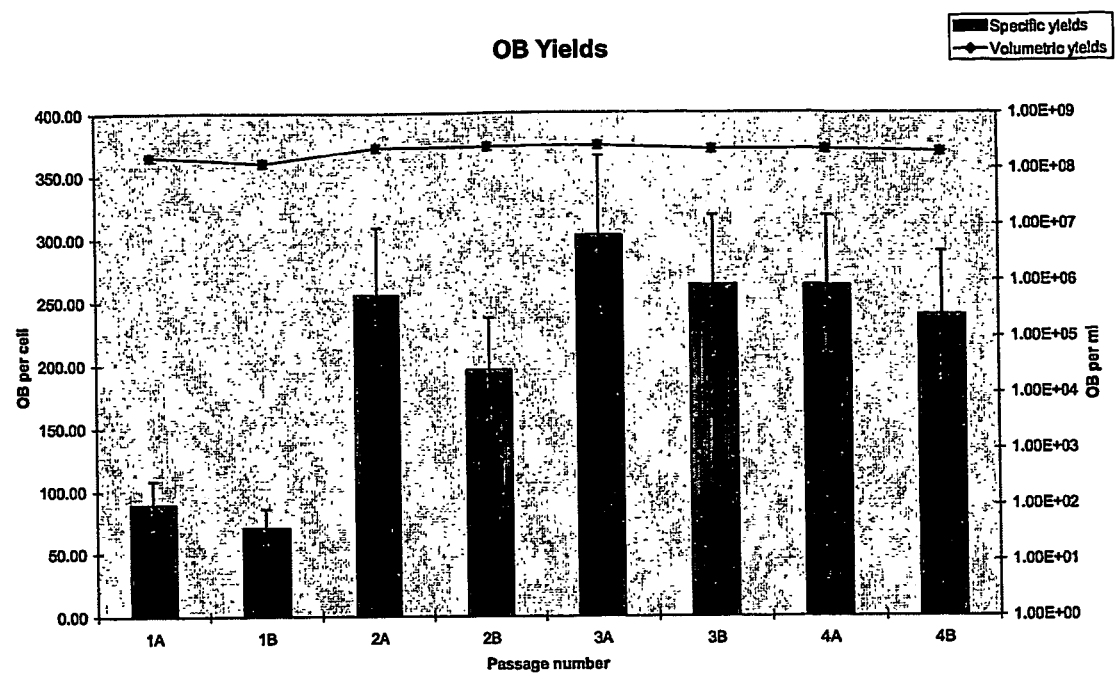
FIG. 4 shows the OB yield over 4 passages using two samples (flasks A and B).

The preferred embodiment of the method for producing large quantities of baculovirus involves a two step process of initially producing virus in caterpillar larvae and then using occlusion derived virus from a caterpillar larvae to inoculate a cell culture and allow a limited number of serial passages of the cell culture (see FIG. 1).

The method initially involves preparing master and working stocks of caterpillar larvae occlusion bodies. The master and working stocks of caterpillar OB are prepared by feeding large *Helicoverpa armigera* larvae approximately 1,000 OB each. As they die (6-10 days post infection) they are collected and stored at 4° C. Approximately 1.5-2 larvae are required for a 10 litre (passage 1) inoculum as $2.5 \times 10^{10}$ OB are required per run and approximately $1.7 \times 10^{10}$ OB are produced per larvae. After a sufficient number of dead caterpillars are pooled, they are extracted with SDS (30 minutes, 0.5% final concentration), homogenized (blender process), filtered (cheesecloth), spun down and suspended in water ($10^{10}$ OB/ml). A number of water washes can be carried out to help remove excess debris. The OB suspension can be stored refrigerated or frozen.

The OB are extracted using the VPM3 extraction method which includes the steps of adding 40 μl of alkaline solution (0.5 M $Na_2CO_3$, 1 M NaCl) for each 0.7 ml OB suspension ($10^{10}$ OB/ml), the mixture is well mixed and incubated at 28° C. for 30 minutes. The incubated OB mixture is then diluted with 10 ml of VPM3 media for each 0.74 ml of extracted OB (see FIG. 2 for formulation of VPM3). The diluted ODV suspension is then filter sterilized through a 0.22 μm filter. The resultant ODV suspension is then used as inoculum.

FIG. 3 shows examples of yields of OB per cell used for extraction and resultant yield of OB per cell at passage 4.

Approximately $2.5 \times 10^{10}$ OB are required to produce enough ODV for use as an inoculum to infect a 10 litre culture ($5 \times 10^5$ cells/ml).

The baculovirus inoculated 10 litre culture was aerobically incubated in a bioreactor at 28° C. for approximately 3 days. The incubation is passage 1. The fermentation was gradually scaled up so that passages 2, 3 and 4 were 100 litres, 1,000 litres and 10,000 litres respectively. All the incubations were aerated at 28° C. for approximately 2 days, except the final incubation which was for 10-15 days.

The 10,000 litre culture has an approximate cell density between $1.5$-$2.0 \times 10^9$ cells per litre and $2.5 \times 10^{11}$ OB per litre (which is approximately 150 OB per cell). The OB had a LC50 against *Helicoverpa* spp caterpillars of 0.2-1.0 OB per $mm^2$.

In a further example shown in FIG. 4, $10^{11}$ OB were successfully extracted and filtered. The filtered sterilized extraction was sampled to infect duplicate 100 ml cultures (flasks A and B). The OB yields after passage 4 (10,000 litre culture) were relatively high with 263 and 239 OB per cell obtained from flasks A and B respectively.

Variations

It will of course be realised that while the foregoing has been given by way of illustrative example of this invention, all such and other modifications and variations thereto as would be apparent to persons skilled in the art are deemed to fall within the broad scope and ambit of this invention as is herein set forth.

Throughout the description and claims this specification the word "comprise" and variations of that word such as "comprises" and "comprising", are not intended to exclude other additives, components, integers or steps.

The invention claimed is:

1. A method of producing large quantities of baculovirus including
   inoculating caterpillar larvae with a baculovirus inoculum;
   incubating inoculated caterpillar larvae;
   harvesting baculovirus occlusion bodies (OBs) from the infected caterpillar larvae;
   extracting occlusion derived virus from the occlusion bodies;
   inoculating a culture of host insect cells with an inoculum of occlusion derived virus;
   incubating virus/cell culture; and
   harvesting baculovirus from the incubated virus/cell culture, wherein the incubation of the virus/cell culture is for a period of time that enables four or five passages of baculovirus.

2. A method of producing large quantities of baculovirus as claimed in claim 1, wherein the baculovirus is selected from any one of the following group: *Helicoverpa armigera* SNPV, *Helicoverpa zea* SNPV, *Spodoptera frugiperda* MNPV, *Anticarsia gemmatalis* MNPV, *Autographa californica* MNPV, *Anagrapha falcifera* MNPV, *Lymantria dispar* MNPV, *Bombyx mori* MNPV, *Spodoptera exigua* MNPV, *Trichoplusia ni* MNPV, *Orgyia pseudotsugata* MNPV and *Buzura suppressaria* SNPV.

3. A method of producing large quantities of baculovirus as claimed in claim 1, wherein the baculovirus is a *Helicoverpa armigera* isolate.

4. A method of producing large quantities of baculovirus as claimed in claim 1, wherein there is more than one step of producing baculovirus from larvae in order to produce a suitable amount of occlusion bodies working stock, and the suitable amount of occlusion bodies working stock has approximately $2\times10^{12}$ occlusion bodies.

5. A method of producing large quantities of baculovirus as claimed in claim 1, wherein the occlusion derived virus (ODV) is inoculated in the cell culture at an MOI that can be as low as $2.5\times10^{10}$ occlusion bodies to $5\times10^{5}$ cells per ml.

6. A method of producing large quantities of baculovirus as claimed in claim 1, wherein an inoculum of occlusion derived virus is obtained from as low as $2.5\times10^{10}$ occlusion bodies and introduced into a ten liter bioreactor containing $5\times10^5$ cells per ml, the culture is then progressively scaled up from a 10 liter volume (P1) to a 100 liter volume (P2), then to a 1,000 liter volume (P3) and finally a 10,000 liter volume (P4); wherein the 10 liter culture producea approximately $10^7$ PFU (Baculovirus) per ml, the 10,000 liter cultuer has an approximate cell density between $1.5$-$2.0 \times10^9$ cells per liter and a $2.5\times10^{11}$ OB per liter (which is approximately 150 OB per cell) and the OB has a LC50 against heliothis caterpillars of between 0.2-1 0 OB per $mm^2$.

7. A method of producing large quantities of baculovirus as claimed in claim 1, wherein the occlusion derived virus is extracted using alkali to lyse the occlusion bodies and the resultant viral particles are stabilized in an appropriate buffering media.

8. A method of producing large quantities of baculovirus as claimed in claim 1, wherein the method of extraction includes mixing an alkaline solution with an OB suspension and incubating the mixture for a period of time and at a temperature that separates the viral particles, the ODV are then suspended in VPM3 stabilizing media; the ODV is extracted without the use of a trypsin treatment and without the use of serum.

9. A method of producing large quantities of baculovirus as claimed in claim 4, wherein the baculovirus are produced from larvae in an initial step to form an occlusion bodies master stock, the occlusion bodies master stock is then used to provide inoculum for the production of occlusion bodies working stocks.

10. A method of producing large quantities of baculovirus as claimed in claim 9, wherein an inculum of extracted occlusion derived virus has approximately $2\times10^{12}$ occlusion bodies whereas the baculovirus inoculum for the initial step has approximately $10^9$ occlusion bodies.

* * * * *